(12) United States Patent
Kawanaka (10) Patent No.: US 11,443,845 B2
(45) Date of Patent: Sep. 13, 2022

(54) SYSTEMS AND METHODS FOR STORING COMPRESSED IMAGES

(71) Applicant: FUJIFILM MEDICAL SYSTEMS U.S.A., INC., Morrisville, NC (US)

(72) Inventor: Tatsuo Kawanaka, Tokyo (JP)

(73) Assignee: FUJIFILM MEDICAL SYSTEMS U.S.A., INC., Morrisville, NC (US)

( * ) Notice: Subject to any disclaimer, the term of this patent is extended or adjusted under 35 U.S.C. 154(b) by 333 days.

(21) Appl. No.: 16/883,516

(22) Filed: May 26, 2020

(65) Prior Publication Data

US 2021/0375434 A1    Dec. 2, 2021

(51) Int. Cl.
| | |
|---|---|
| *G16H 30/20* | (2018.01) |
| *G16H 10/60* | (2018.01) |
| *G06T 9/00* | (2006.01) |
| *G06T 7/00* | (2017.01) |

(52) U.S. Cl.
CPC ............ *G16H 30/20* (2018.01); *G06T 7/0014* (2013.01); *G06T 9/00* (2013.01); *G16H 10/60* (2018.01); *G06T 2207/30016* (2013.01)

(58) Field of Classification Search
CPC ...... G16H 30/20; G16H 10/60; G06T 7/0014; G06T 9/00
See application file for complete search history.

(56) References Cited

U.S. PATENT DOCUMENTS

| | | | |
|---|---|---|---|
| 10,361,802 B1 * | 7/2019 | Hoffberg-Borghesani | ................. G06F 3/00 |
| 2004/0120557 A1 | 6/2004 | Sabol et al. | |
| 2004/0122702 A1 | 6/2004 | Sabol et al. | |
| 2004/0122703 A1 | 6/2004 | Walker et al. | |
| 2004/0122705 A1 | 6/2004 | Sabol et al. | |
| 2004/0122706 A1 | 6/2004 | Walker et al. | |
| 2004/0122707 A1 | 6/2004 | Sabol et al. | |

(Continued)

FOREIGN PATENT DOCUMENTS

| | | |
|---|---|---|
| JP | 2018-116699 A | 7/2018 |
| WO | WO 2004/061742 A2 | 7/2004 |

(Continued)

*Primary Examiner* — Edward Park
(74) *Attorney, Agent, or Firm* — Baker Botts L.L.P.

(57) ABSTRACT

Method for storing a compressed digital image includes performing an artificial intelligence ("AI") diagnostic test on the digital image; determining an uncompressed diagnostic result associated with the digital image based on the AI diagnostic test; generating one or more compressed digital images by compressing the digital image, each compressed digital image having a respective compression ratio; decompressing each compressed digital image to generate a respective decompressed digital image; performing the diagnostic test on each decompressed digital image; determining a decompressed diagnostic result associated with each decompressed digital image based on the respective diagnostic test; identifying one or more decompressed digital images having a respective decompressed diagnostic result that is the same as the uncompressed diagnostic result; selecting from the identified one or more decompressed digital images, the decompressed digital image associated with the highest compression ratio; and storing the compressed digital image associated with the selected decompressed digital image.

24 Claims, 10 Drawing Sheets

(56) References Cited

U.S. PATENT DOCUMENTS

| | | |
|---|---|---|
| 2004/0122709 A1 | 6/2004 | Avinash et al. |
| 2004/0122719 A1 | 6/2004 | Sabol et al. |
| 2004/0122790 A1 | 6/2004 | Walker et al. |
| 2007/0118399 A1 | 5/2007 | Avinash et al. |
| 2018/0204639 A1 | 7/2018 | Konishi et al. |

FOREIGN PATENT DOCUMENTS

| | | |
|---|---|---|
| WO | WO 2004/061743 A2 | 7/2004 |
| WO | WO 2004/061744 A2 | 7/2004 |

* cited by examiner

SYSTEMS AND METHODS FOR STORING COMPRESSED IMAGES

BACKGROUND

1. Field of Disclosed Subject Matter

The disclosed subject matter is directed to systems and methods for storing compressed images, for example, medical images and more specifically Digital Imaging and Communications in Medicine ("DICOM") Objects. The systems and methods described herein can maximize compression ratio using lossy compression while keeping diagnostic quality.

2. Description of Related Art

In medical imaging, Picture Archiving and Communication Systems ("PACS") are a combination of computers and networks dedicated to the storage, retrieval, presentation, and distribution of images. While medical information can be stored in a variety of formats, a common format of image storage is DICOM. DICOM is a standard in which, among other things, medical images and associated meta-data can be communicated from imaging modalities (e.g., x-ray (or x-rays' digital counterparts: computed radiography ("CR") and digital radiography ("DR")), computed tomography ("CT"), and magnetic resonance imaging ("MRI") apparatuses) to remote storage and/or client devices for viewing and/or other use.

With increases in technical innovation, the medical data generated by imaging modalities is getting larger. For example, new technologies can lead to additional medical images for patients, and improved technology can lead to medical images with more detail and, as a result, larger file sizes. Although the additional data can be helpful for more accurate medical diagnostics, it can require increased space for storage and archiving. Accordingly, it can be beneficial to compress files to reduce file size and facilitate storage.

Files can be compressed using loss-less compression (i.e., no data is lost when the file is compressed and then decompressed) or using lossy compression (i.e., some data is lost when the file is compressed and then decompressed). Loss-less compression and lossy compression can each include to a variety of compression techniques. Lossy compression techniques can reduce image size and/or vary the amount of compression, and can result in various amounts of lost data. While lossy compression can generally reduce file size more than loss-less compression, which can make storage more efficient, lossy compression can result in lost information. As an example, if a medical image is compressed using lossy compression, the quality of the medical image after lossy compression and decompression can be reduced, and the diagnostic value of the file can be reduced or lost. For example, if an image quality is degraded after lossy compression and decompression, it can become difficult or impossible to identify certain features of the image and therefore it can become difficult or impossible to use the image to make a medical diagnosis.

Accordingly, there is a need for systems and methods for compressing and storing medical images, for example, using lossy compression, without reducing the quality of the medical images such that the medical images are no longer medically useful, for example, for making medical diagnoses.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended figures.

To achieve these and other advantages and in accordance with the purpose of the disclosed subject matter, as embodied and broadly described, the disclosed subject matter is directed to systems and methods for storing compressed images. For example, a method for storing a compressed digital image includes receiving, at one or more computing devices, a digital image; performing, at the one or more computing devices, an artificial intelligence ("AI") diagnostic test on the digital image; determining, at the one or more computing devices, an uncompressed diagnostic result associated with the digital image based on the AI diagnostic test; generating, at the one or more computing devices, one or more compressed digital images by compressing the digital image, each compressed digital image having a respective compression ratio; decompressing, at the one or more computing devices, each compressed digital image to generate a respective decompressed digital image; performing, at the one or more computing devices, the AI diagnostic test on each decompressed digital image; determining, at the one or more computing devices, a decompressed diagnostic result associated with each decompressed digital image based on the respective AI diagnostic test; identifying, at the one or more computing devices, one or more decompressed digital images having a respective decompressed diagnostic result that is the same as the uncompressed diagnostic result; selecting, at the one or more computing devices and from the identified one or more decompressed digital images, the decompressed digital image associated with the highest compression ratio; and storing, at the one or more computing devices, the compressed digital image associated with the selected decompressed digital image.

The digital record can be a medical image record. The medical image record can be a DICOM Service-Object Pair Instance. Each compressed digital image can be generated using a respective loss-less or lossy compression technique. For each compressed digital image, the compression ratio can be calculated by dividing an uncompressed file size of the uncompressed image by a compressed file size of the compressed digital image.

The method can include deleting the digital image. The method can include deleting the selected decompressed digital image, and the method can include deleting each non-selected decompressed digital image and each associated compressed digital image.

In accordance with the disclosed subject matter, one or more computer-readable non-transitory storage media embodying software are provided. The software can be operable when executed to: receive a digital image; perform an AI diagnostic test on the digital image; determine an uncompressed diagnostic result associated with the digital image based on the AI diagnostic test; generate one or more compressed digital images by compressing the digital image, each compressed digital image having a respective compression ratio; decompress each compressed digital image to generate a respective decompressed digital image; perform the AI diagnostic test on each decompressed digital image; determine a decompressed diagnostic result associated with each decompressed digital image based on the respective AI diagnostic test; identify one or more decompressed digital images having a respective decompressed diagnostic result that is the same as the uncompressed diagnostic result; select from the identified one or more decompressed digital images, the decompressed digital image associated with the highest compression ratio; and store the compressed digital image associated with the selected decompressed digital image.

In accordance with the disclosed subject matter, a system including one or more processors; and a memory coupled to the processors including instructions executable by the processors are provided. The processors can be operable when executing the instructions to: receive a digital image; perform an AI diagnostic test on the digital image; determine an uncompressed diagnostic result associated with the digital image based on the AI diagnostic test; generate one or more compressed digital images by compressing the digital image, each compressed digital image having a respective compression ratio; decompress each compressed digital image to generate a respective decompressed digital image; perform the AI diagnostic test on each decompressed digital image; determine a decompressed diagnostic result associated with each decompressed digital image based on the respective AI diagnostic test; identify one or more decompressed digital images having a respective decompressed diagnostic result that is the same as the uncompressed diagnostic result; select from the identified one or more decompressed digital images, the decompressed digital image associated with the highest compression ratio; and store the compressed digital image associated with the selected decompressed digital image.

DETAILED DESCRIPTION

Figure 1:
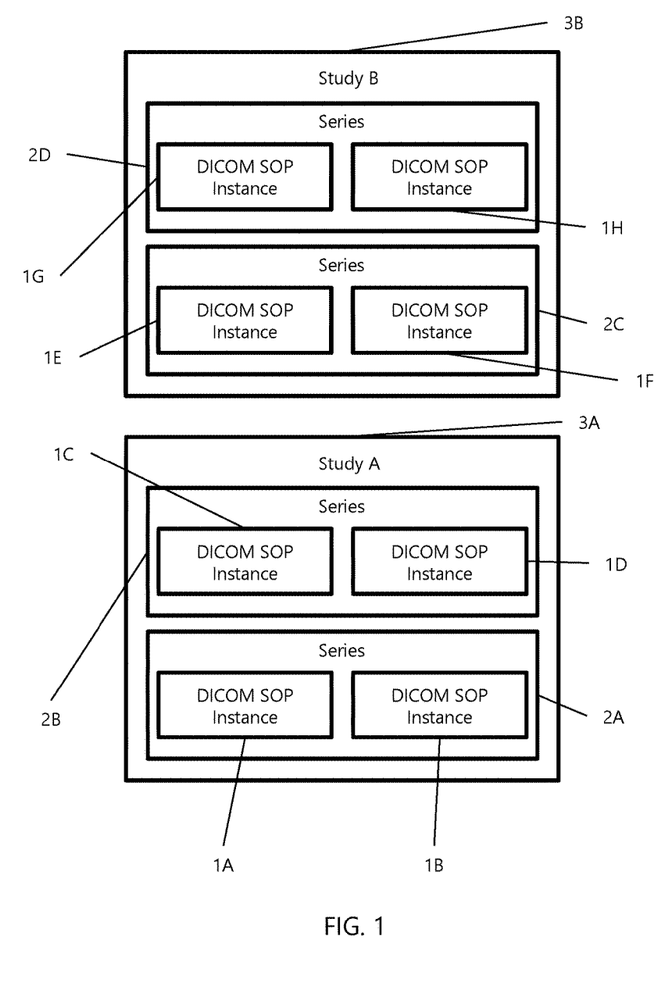
FIG. 1 shows a hierarchy of medical image records that can be compressed and stored in accordance with the disclosed subject matter.

Reference will now be made in detail to various exemplary embodiments of the disclosed subject matter, exemplary embodiments of which are illustrated in the accompanying figures. For purpose of illustration and not limitation, the systems and methods are described herein with respect to compressing and storing digital records, and particularly, digital medical image records (also referred to as "medical image records"), specifically DICOM records. However, the methods and systems described herein can be used for compressing and storing any digital records (medical or otherwise). As used in the description and the appended claims, the singular forms, such as "a," "an," "the," and singular nouns, are intended to include the plural forms as well, unless the context clearly indicates otherwise. Accordingly, as used herein, the term medical image record can refer to one medical image record, or a plurality of medical image records. For example, and with reference to FIG. 1 for purpose of illustration and not limitation, as referred to herein a medical image record can include a single DICOM SOP Instance (also referred to as "DICOM Instance" and "DICOM image") 1 (e.g., 1A-1H), one or more DICOM SOP Instances 1 (e.g., 1A-1H) in one or more Series 2 (e.g., 2A-D), one or more Series 2 (e.g., 2A-D) in one or more Studies 3 (e.g., 3A, 3B), and one or more Studies 3 (e.g., 3A, 3B). The methods and systems described herein can be used with medical image records stored on PACS, however, a variety of records are suitable for the present disclosure and records can be stored in any system, for example a Vendor Neutral Archive ("VNA").

Referring to FIGS. 2-7 for purpose of illustration and not limitation, the disclosed system 100 can be configured to compress and store a medical image record 10 including one or more of DICOM images 1 (e.g., 1J). Particularly, System 100 can compress and store the DICOM Images 1 (e.g., 1J) without reducing the quality of the DICOM Images 1 (e.g., 1J) such that the DICOM Images 1 (e.g., 1J) are no longer medically useful, for example, for making medical diagnoses or for comparison with other DICOM Images 1 (e.g., 1A-1K) to understand a patient's changes over time. The system 100 can include one or more computing devices defining a server 30 and user workstation 60. The user workstation 60 can be coupled to the server 30 by a network. The network, for example, can be a Local Area Network ("LAN"), a Wireless LAN ("WLAN"), a virtual private network ("VPN"), or any other network that allows for any radio frequency or wireless type connection. For example, other radio frequency or wireless connections can include, but are not limited to, one or more network access technologies, such as Global System for Mobile communication ("GSM"), Universal Mobile Telecommunications System ("UMTS"), General Packet Radio Services ("GPRS"), Enhanced Data GSM Environment ("EDGE"), Third Generation Partnership Project ("3GPP") Technology, including Long Term Evolution ("LTE"), LTE-Advanced, 3G technology, Internet of Things ("IOT"), fifth generation ("5G"), or new radio ("NR") technology. Other examples can include Wideband Code Division Multiple Access ("WCDMA"), Bluetooth, IEEE 802.11b/g/n, or any other 802.11 protocol, or any other wired or wireless connection.

Figure 2:
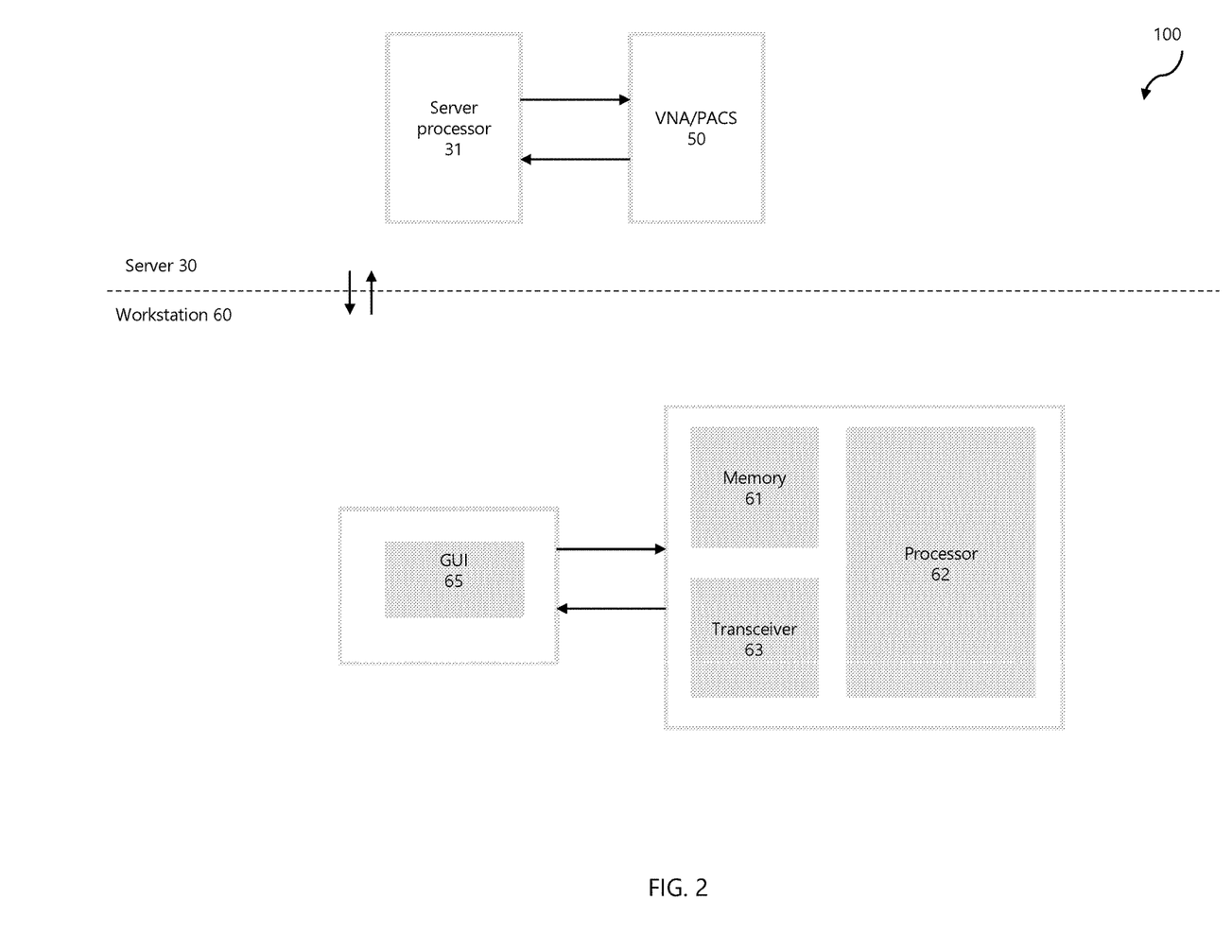
FIG. 2 shows the architecture of a system for compressing and storing medical image records, in accordance with the disclosed subject matter.

Workstation 60 can take the form of any known client device. For example, workstation 60 can be a computer, such as a laptop or desktop computer, a personal data or digital assistant ("PDA"), or any other user equipment or tablet, such as a mobile device or mobile portable media player. Server 30 can be a service point which provides processing, database, and communication facilities. For example, the server 30 can include dedicated rack-mounted servers, desktop computers, laptop computers, set top boxes, integrated devices combining various features, such as two or more features of the foregoing devices, or the like. Server 30 can vary widely in configuration or capabilities, but can include one or more processors, memory, and/or transceivers. Server 30 can also include one or more mass storage devices, one or more power supplies, one or more wired or wireless network interfaces, one or more input/output interfaces, and/or one or more operating systems. Server 30 can include additional data storage such as VNA/PACS 50, remote PACS, VNA, or other vendor PACS/VNA.

A user can be any person authorized to access workstation 60 and/or server 30, including a health professional, medical technician, researcher, or patient. In some embodiments a user authorized to use the workstation 60 and/or communicate with the server 30 can have a username and/or password that can be used to login or access workstation 60 and/or server 30.

Workstation 60 can include GUI 65, memory 61, processor 62, and transceiver 63. Medical image records 10 received by workstation 60 can be processed using one or more processors 62. Processor 62 can be any hardware or software used to execute computer program instructions. These computer program instructions can be provided to a processor of a general purpose computer to alter its function to a special purpose, a special purpose computer, application-specific integrated circuit ("ASIC"), or other programmable digital data processing apparatus, such that the instructions, which execute via the processor of the workstation 60 or other programmable data processing apparatus, implement the functions/acts specified in the block diagrams or operational block or blocks, thereby transforming their functionality in accordance with embodiments herein. The processor 62 can be a portable embedded micro-controller or micro-computer. For example, processor 62 can be embodied by any computational or data processing device, such as a central processing unit ("CPU"), digital signal processor ("DSP"), ASIC, programmable logic devices ("PLDs"), field programmable gate arrays ("FPGAs"), digitally enhanced circuits, or comparable device or a combination thereof. The processor 62 can be implemented as a single controller, or a plurality of controllers or processors.

Workstation 60 can send and receive medical image records 10 from server 30 using transceiver 63. Transceiver 63 can, independently, be a transmitter, a receiver, or both a transmitter and a receiver, or a unit or device that can be configured both for transmission and reception. In other words, transceiver 63 can include any hardware or software that allows workstation 60 to communicate with server 30. Transceiver 63 can be either a wired or a wireless transceiver. When wireless, the transceiver 63 can be implemented as a remote radio head which is not located in the device itself, but in a mast. While FIG. 2 only illustrates a single transceiver 63, workstation 60 can include one or more transceivers 63. Memory 61 can be a non-volatile storage medium or any other suitable storage device, such as a non-transitory computer-readable medium or storage medium. For example, memory 61 can be a random-access memory ("RAM"), read-only memory ("ROM"), hard disk drive ("HDD"), erasable programmable read-only memory ("EPROM"), electrically erasable programmable read-only memory ("EEPROM"), flash memory or other solid-state memory technology. Memory 61 can also be a compact disc read-only optical memory ("CD-ROM"), digital versatile disc ("DVD"), any other optical storage, magnetic cassettes, magnetic tape, magnetic disk storage or other magnetic storage devices, or any other physical or material medium which can be used to tangibly store the desired information or data or instructions and which can be accessed by a computer or processor. Memory 61 can be either removable or non-removable.

Server 30 can include a server processor 31 and VNA/PACS 50. The server processor 31 can be any hardware or software used to execute computer program instructions. These computer program instructions can be provided to a processor of a general purpose computer to alter its function to a special purpose, a special purpose computer, ASIC, or other programmable digital data processing apparatus, such that the instructions, which execute via the processor of the client station or other programmable data processing apparatus, implement the functions/acts specified in the block diagrams or operational block or blocks, thereby transforming their functionality in accordance with embodiments herein. In accordance with the disclosed subject matter, the server processor 31 can be a portable embedded micro-controller or micro-computer. For example, server processor 31 can be embodied by any computational or data processing device, such as a CPU, DSP, ASIC, PLDs, FPGAs, digitally enhanced circuits, or comparable device or a combination thereof. The server processor 31 can be implemented as a single controller, or a plurality of controllers or processors.

Figure 3:
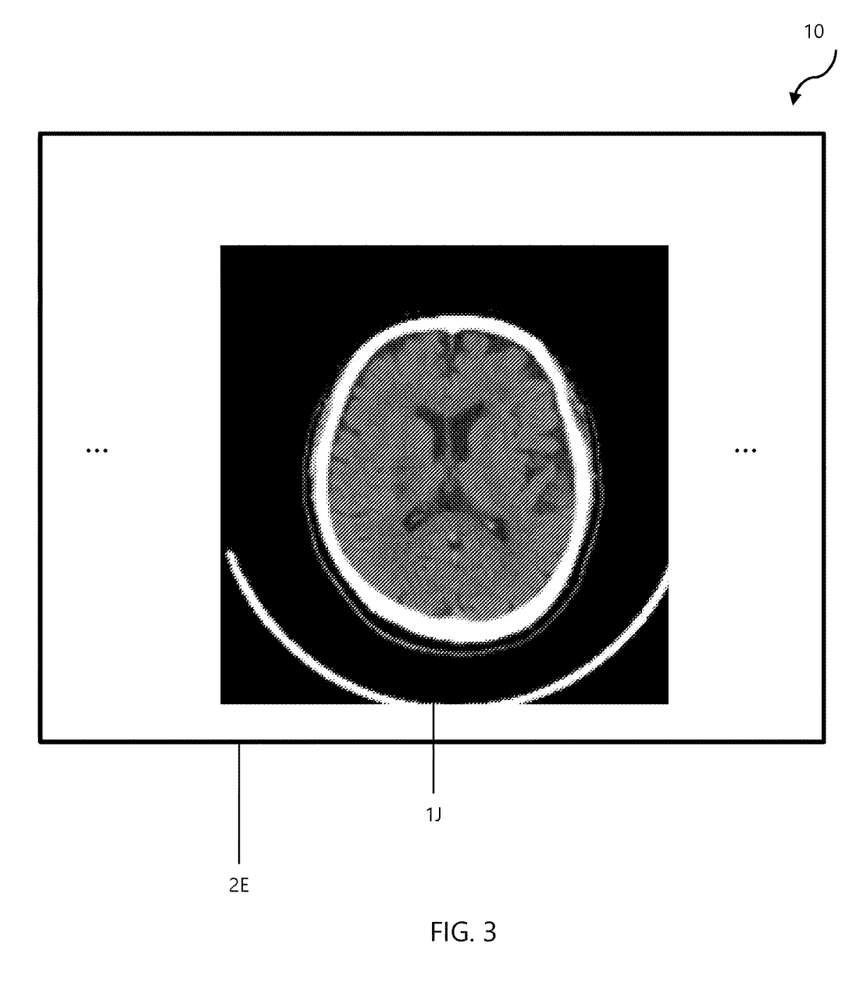
FIG. 3 shows a medical image record that can be compressed and stored in accordance with the disclosed subject matter.

As shown in FIG. 3, for purpose of illustration and not limitation, medical image record 10 can be a Series 2E including a number (for example 100) of DICOM SOP Instances 1 (e.g., 1J). FIG. 3 only shows one DICOM SOP Instance 1J for purpose of clarity. Series 2E can include a plurality of CT brain scans, with each CT brain scan stored as a DICOM SOP Instance 1 (e.g., 1J).

In operation, system 100 can be used to compress and store medical image record 10. Medical image record 10 can be received by workstation 60 and instructions can be provided to workstation 60 to compress and store medical image record 10, and particularly, each DICOM image 1 (e.g., 1J) within Series 2E. Each DICOM image 1 (e.g., 1J) can have an uncompressed file size. For example, DICOM image 1J can have an uncompressed file size of 1 MB (1000 KB). The process is described below with reference to DICOM image 1J, however, the process can be performed for each DICOM image 1 (e.g., 1J) within Series 2E.

Figure 4:
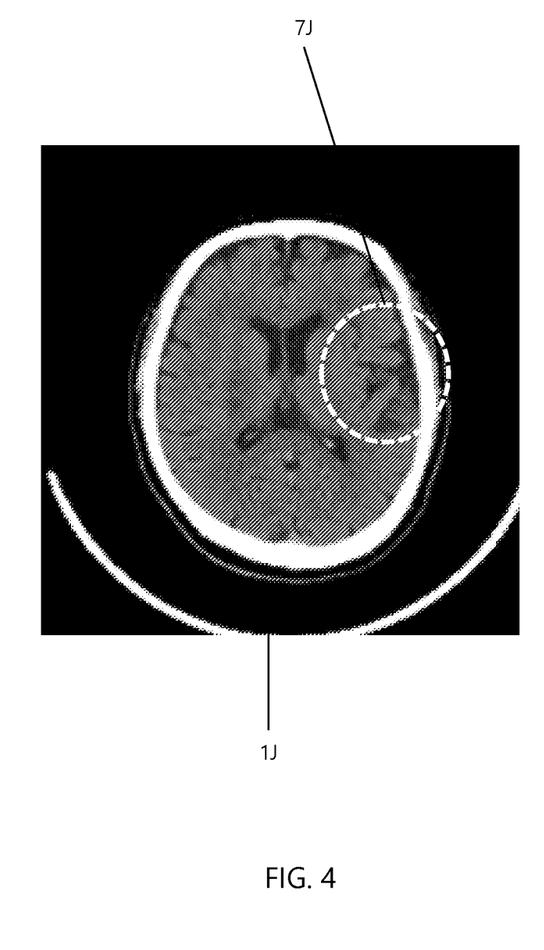
FIG. 4 shows the result of an artificial intelligence diagnostic test performed on a medical image record, in accordance with the disclosed subject matter.
Figure 7:
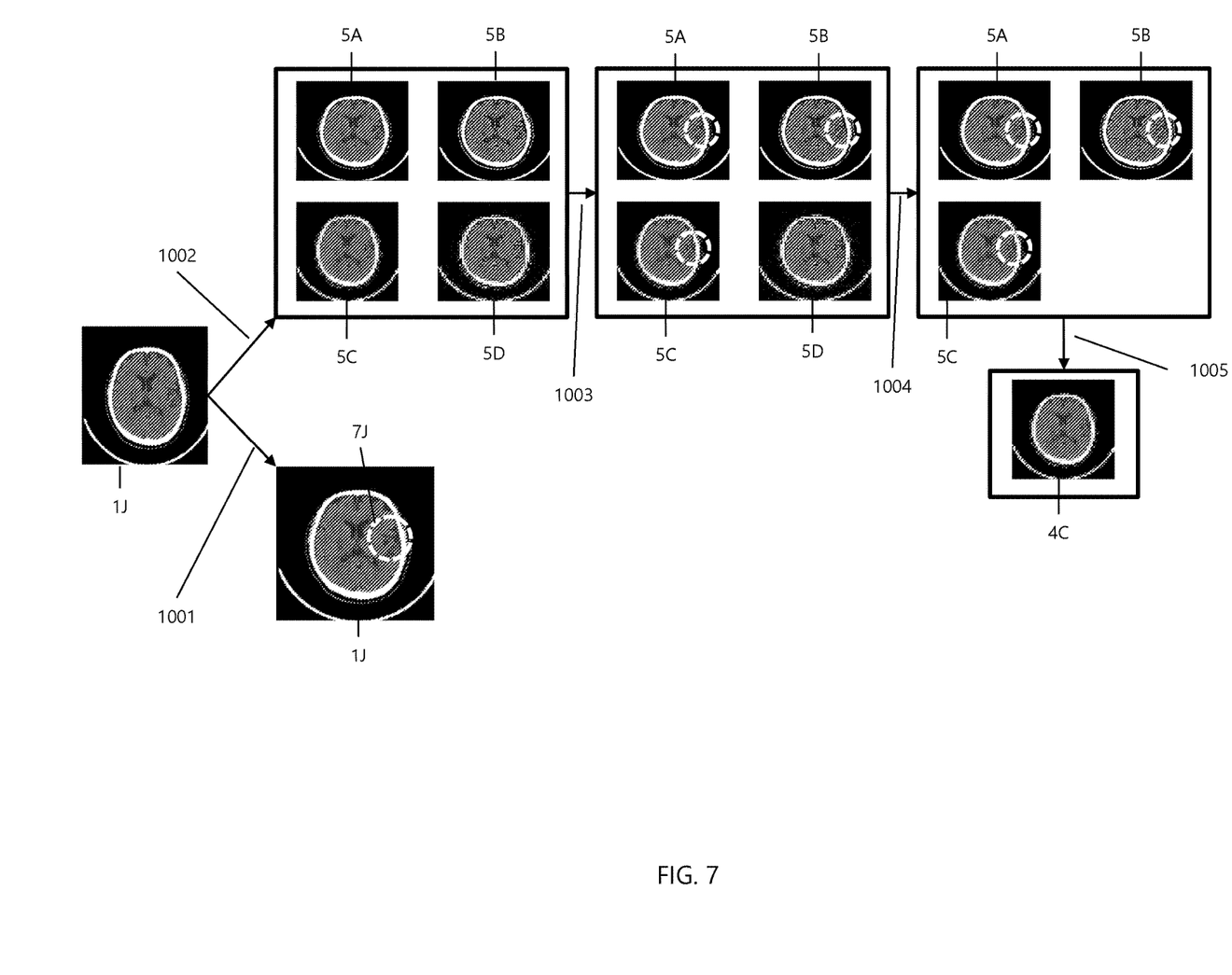
FIG. 7 is a flow chart illustrating how a medical image record can be compressed and stored in accordance with the disclosed subject matter.

To compress and store DICOM image 1J, an AI diagnostic test can be performed on the DICOM image 1J (see e.g., arrow 1001 in FIG. 7). Based at least in part on the AI diagnostic test, workstation 60 can determine an uncompressed diagnostic result associated with the DICOM image 1J. For example, and as shown in FIG. 4, the AI diagnostic test can identify a brain lesion in region 7J of DICOM image 1J. Accordingly, the diagnostic result can be that there is a brain injury at region 7J. As an example, and not by way of limitation, the diagnostic result can include the type of lesion (e.g., intracranial hemorrhage, subarachnoid hemorrhage, or infarction), a measurement of the lesion size (e.g., volume of the hemorrhage for brain images—however compression techniques can be limited to lower compression ratios for measurement of lesion size), and/or any other diagnostic result. In accordance with the disclosed subject matter, the diagnostic result can be confirmed manually, for example, by a medical professional, technician, or other qualified person.

Figure 5:
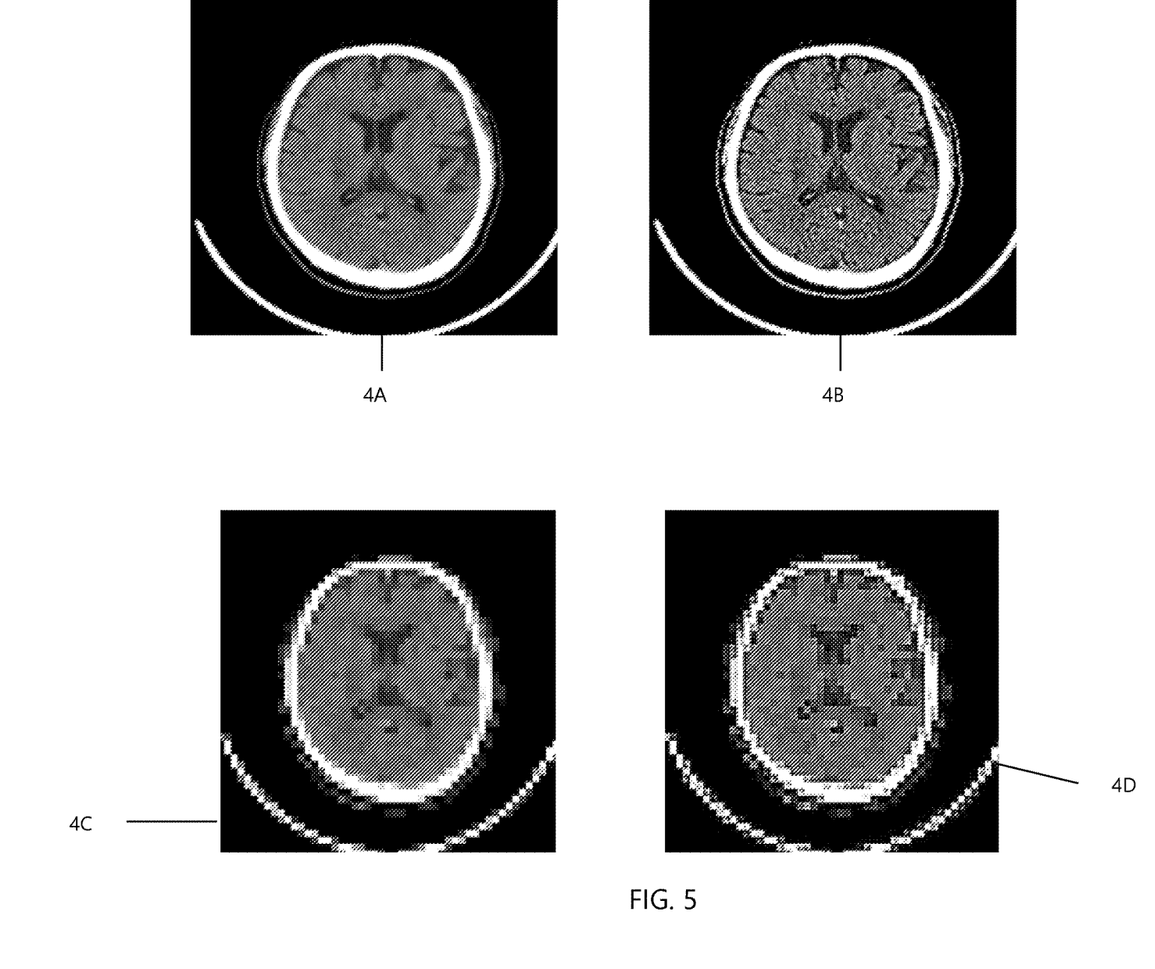
FIG. 5 shows compressed digital images of the medical image record of FIG. 4.
Figure 6:
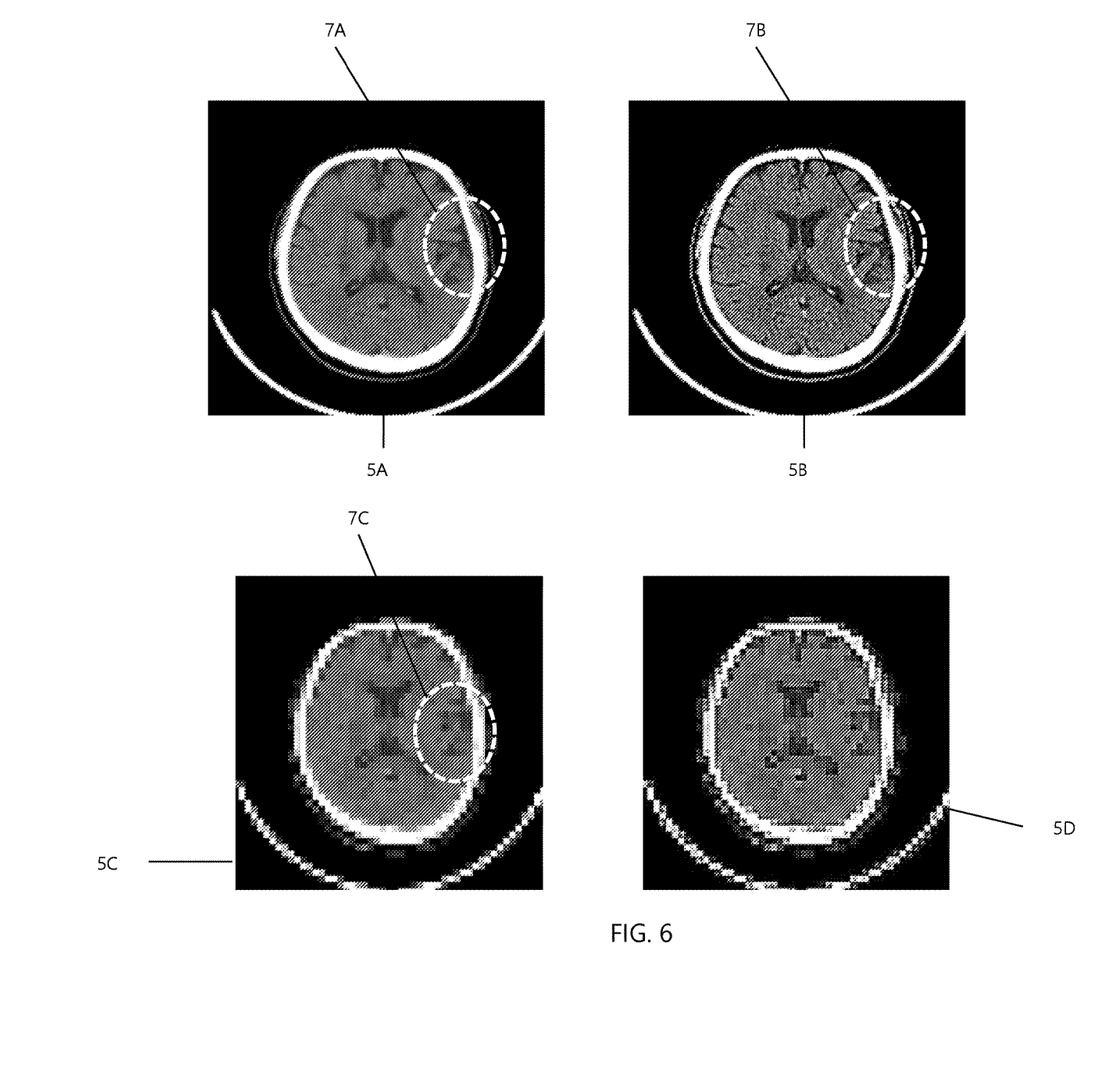
FIG. 6 shows decompressed digital images of the compressed digital images of FIG. 4, including results of an artificial intelligence diagnostic test performed on each, in accordance with the disclosed subject matter.

System 100 can generate one or more compressed digital images 4 (e.g., 4A-4D) by compressing DICOM image 1J and can generate a decompressed digital image 5 (e.g., 5A-5D) for each compressed digital image 4 (e.g., 4A-4D) (see e.g., arrow 1002 in FIG. 7). While four compressed digital images 4 (e.g., 4A-4D) and respective decompressed digital images 5 (e.g., 5A-5D) are shown, system 100 can generate any number of compressed and decompressed digital images. Each compressed digital image 4 (e.g., 4A-4D) can be compressed using a different compression technique. Examples of compression techniques can include JPEG, wavelet compression (e.g., JPEG2000 or other private implementations), and run length encoding ("RLE"). For example, compressed digital image 4A can be compressed using a loss-less compression. Compressed digital image 4A can have a compressed file size of 800 KB. Compressed digital image 4B can be compressed using a lossy compression technique, and can result in a loss of 10% of the original data (referred to as 90% lossy). Compressed digital image 4B can have a compressed file size of 500 KB. Compressed digital image 4C can be compressed using a lossy compression technique, and can result in a loss of 20% of the original data (referred to as 80% lossy). Compressed digital image 4C can also reduce the image size, for example by one quarter of the original size. Compressed digital image 4C can have a compressed file size of 200 KB. Compressed digital image 4D can be compressed using a lossy compression technique, and can result in a loss of 30% of the original data (referred to as 70% lossy). Compressed digital image 4D can also reduce the image size, for example by one quarter of the original size. Compressed digital image 4D can have a compressed file size of 100 KB. A compression ratio can be calculated for each compressed digital image 4 (e.g., 4A-4D) by dividing the uncompressed file size of DICOM image 1J by a compressed file size of each compressed digital image 4 (e.g., 4A-4D), respectively. For each compressed digital image 4 (e.g., 4A-4D), system 100 can generate a decompressed digital image 5 (e.g., 5A-5D) by decompressing the respective compressed digital image 4 (e.g., 4A-4D). For example, decompressed digital image 5A can be associated with compressed digital image 4A; decompressed digital image 5B can be associated with compressed digital image 4B; decompressed digital image 5C can be associated with compressed digital image 4C; and decompressed digital image 5D can be associated with compressed digital image 4D. The chart below provides the details of each image.

in decompressed digital image 5B, and region 7C in decompressed digital image 5C. Accordingly, the diagnostic result for each of decompressed digital images 5A, 5B, and 5C can be that there is a brain injury at regions 7A, 7B, and 7C, respectively. As shown in FIG. 6, the AI diagnostic test cannot identify a brain lesion in decompressed digital image 5D and accordingly the diagnostic result for decompressed digital image 5D is a healthy brain.

System 100 can identify one or more decompressed digital images 5 (e.g., 5A-C) having the same diagnostic result as DICOM Image 7J (see e.g., arrow 1004 in FIG. 7). For example, decompressed digital images 5A, 5B, and 5C can be identified because decompressed digital images 5A, 5B, and 5C, have the same diagnostic result as DICOM Image 1J (i.e., a brain legion in regions 7A, 7B, and 7C, respectively). System can select the decompressed digital image 5 (e.g., 5A-5C) associated with the highest compression ratio and can store the associated compressed digital image 4 (e.g., 4A-4C) (see e.g., arrow 1005 in FIG. 7). For example, of the identified decompressed digital images 5A, 5B, and 5C, decompressed digital image 5C is associated with highest compression ratio. That is, decompressed digital image 5A is associated with compressed digital image 4A and a compression ratio of 1.25; decompressed digital image 5B is associated with compressed digital image 4B and a compression ratio of 2; and decompressed digital image 5C is associated compressed digital image 4C and a compression ratio of 5. Accordingly, compressed digital image 4C, which is associated with decompressed digital image 5C can be stored. Compressed digital image 4C can be stored on workstation 60 or server 30, for example in VNA/PACS 50. In accordance with the disclosed subject matter, system 100 can delete the original DICOM Image 1J, the decompressed digital images 5 (e.g., 5A-5D), and each non-selected compressed digital image 4 (e.g., 4A, 4B, and 4D).

Compressed digital image 4C is the compressed digital image 4 (e.g., 4A-4D) with the highest compression ratio, and therefore the smallest file size, of all the compressed digital images (e.g., 4A-4D) that still maintains enough data to provide a proper diagnosis. As such, the systems and methods described herein can be used to compress medical

| Compressed Image | Decompressed image | Compression Image Quality | Image Size reduction | File size | Compression Ratio |
|---|---|---|---|---|---|
| DICOM Image 1J | DICOM Image 1J | Original | Original | 1000 KB | N/A |
| Compressed digital image 4A | Decompressed digital image 5A | Loss-less | Original | 800 KB | 1.25 |
| Compressed digital image 4B | Decompressed digital image 5B | 90% lossy | Original | 500 KB | 2 |
| Compressed digital image 4C | Decompressed digital image 5C | 80% lossy | ¼ | 200 KB | 5 |
| Compressed digital image 4D | Decompressed digital image 5D | 70% lossy | ¼ | 100 KB | 10 |

System 100 can perform the same AI diagnostic test performed on the DICOM Image 1J on each of the decompressed digital image 5 (e.g., 5A-5D) and the system can determine a decompressed diagnostic result associated with each decompressed digital image 5 (e.g., 5A-5D) (see e.g., arrow 1003 in FIG. 7). For example, and as shown in FIG. 6, the AI diagnostic test can identify a brain lesion in each of region 7A of decompressed digital image 5A, region 7B images as small as possible (including losing some information) and store medical images without reducing the quality of the medical images such that the medical images are no longer medically useful.

In accordance with the disclosed subject matter, the method can be repeated for each DICOM Image 1 (e.g., 1J) within Series 2E. Accordingly, each DICOM Image 1 (e.g., 1J) within Series 2E can be compressed and stored without reducing the quality of a given DICOM Image 1 (e.g., 1J) such that the DICOM Image 1 (e.g., 1J) is no longer medically useful. Different DICOM Images 1 (e.g., 1J) can be compressed using different compression techniques (including loss-less or lossy compression) with each still maintaining the information required to be medically useful. For example, different DICOM Images 1 (e.g., 1J) within Series 2E can be compressed with different amounts of data loss (e.g., loss-less, 90% lossy, 80% lossy, or more). In accordance with the disclosed subject matter, when the uncompressed diagnostic result of a DICOM Image 1 (e.g., 1J) is healthy, the compression technique with the largest compression ratio can be used to compress and store the DICOM Image 1 (e.g., 1J).

Figure 8:
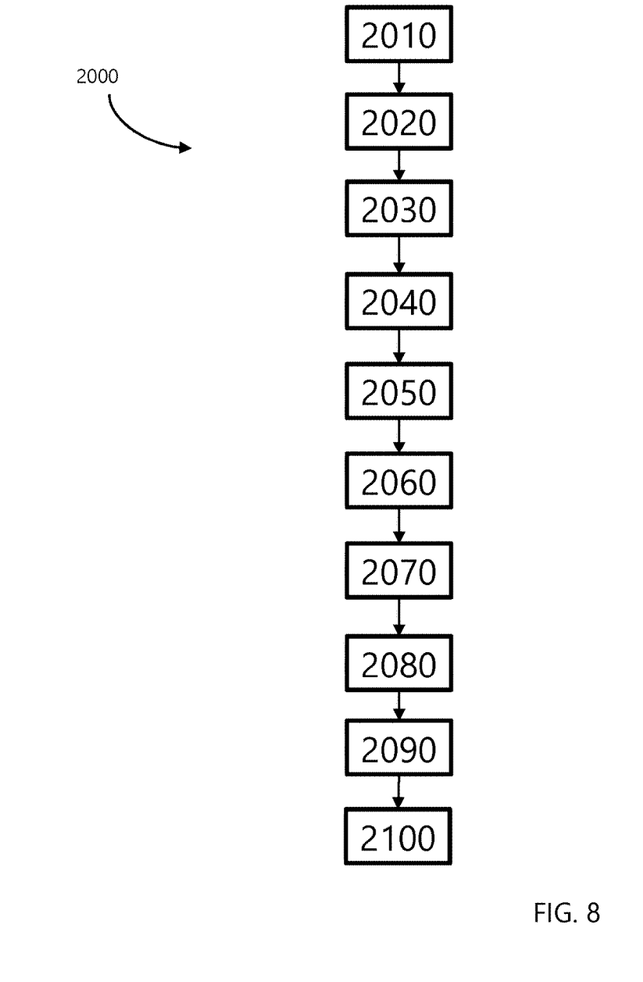
FIG. 8 is a flow chart of a method for storing a compressed digital image in accordance with the disclosed subject matter.

FIG. 8 illustrates an example method 2000 for storing a compressed digital image. The method can begin at step 2010, where the method includes receiving, at one or more computing devices, a digital image. At step 2020 the method can include performing, at the one or more computing devices, an AI diagnostic test on the digital image. At step 2030 the method can include determining, at the one or more computing devices, an uncompressed diagnostic result associated with the digital image based on the AI diagnostic test. At step 2040 the method can include generating, at the one or more computing devices, one or more compressed digital images by compressing the digital image, each compressed digital image having a respective compression ratio. At step 2050 the method can include decompressing, at the one or more computing devices, each compressed digital image to generate a respective decompressed digital image. At step 2060 the method can include performing, at the one or more computing devices, the AI diagnostic test on each decompressed digital image. At step 2070 the method can include determining, at the one or more computing devices, a decompressed diagnostic result associated with each decompressed digital image based on the respective AI diagnostic test. At step 2080 the method can include identifying, at the one or more computing devices, one or more decompressed digital images having a respective decompressed diagnostic result that is the same as the uncompressed diagnostic result. At step 2090, the method can include selecting, at the one or more computing devices and from the identified one or more decompressed digital images, the decompressed digital image associated with the highest compression ratio. At step 2100 the method can include storing, at the one or more computing devices, the compressed digital image associated with the selected decompressed digital image. In accordance with the disclosed subject matter, the method can repeat one or more steps of the method of FIG. 8, where appropriate. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates an example method for storing a compressed digital image including the particular steps of the method of FIG. 8, this disclosure contemplates any suitable method for storing a compressed digital image including any suitable steps, which can include all, some, or none of the steps of the method of FIG. 8, where appropriate. Furthermore, although this disclosure describes and illustrates particular components, devices, or systems carrying out particular steps of the method of FIG. 8, this disclosure contemplates any suitable combination of any suitable components, devices, or systems carrying out any suitable steps of the method of FIG. 8.

Figure 9:
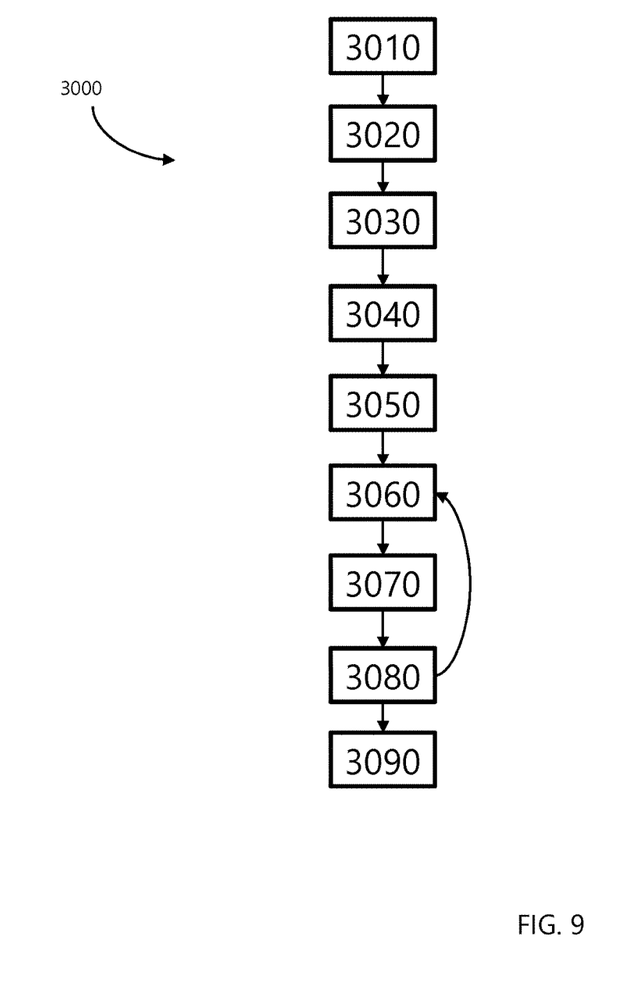
FIG. 9 is a flow chart of a method for storing a compressed digital image in accordance with the disclosed subject matter.

FIG. 9 illustrates an example method 3000 for storing a compressed digital image. The method can include loops and if/then statements to proceed efficiently. For example, the method can being at step 3010, where the method includes receiving, at one or more computing devices, a digital image. At step 3020 the method can include performing, at the one or more computing devices, an AI diagnostic test on the digital image. At step 3030 the method can include determining, at the one or more computing devices, an uncompressed diagnostic result associated with the digital image based on the AI diagnostic test. At step 3040 the method can include generating, at the one or more computing devices, one or more compressed digital images by compressing the digital image, each compressed digital image having a respective compression ratio. At least one of the compressed digital images can be created using a loss-less compression technique. At step 3050 the method can include decompressing, at the one or more computing devices, each compressed digital image to generate a respective decompressed digital image. At step 3060 the method can include performing, at the one or more computing devices, the AI diagnostic test on a first decompressed digital image associated with the lowest compression ratio. At step 3070 the method can include determining, at the one or more computing devices, a decompressed diagnostic result associated with the first decompressed digital image based on the AI diagnostic test. At step 3080 the method can include determining whether the decompressed diagnostic result is the same as the uncompressed diagnostic result. If the result is the same, the method can include storing decompressed digital image as a selected decompressed digital image, return to step 3060 and proceed with the digital image associated with the next lowest compression ratio. If the result is not the same, the method can proceed to step 3090. At step 3090, the method can include storing, at the one or more computing devices, the compressed digital image associated with the selected decompressed digital image. In accordance with the disclosed subject matter, the method can repeat one or more steps of the method of FIG. 9, where appropriate. Although this disclosure describes and illustrates particular steps of the method of FIG. 9 as occurring in a particular order, this disclosure contemplates any suitable steps of the method of FIG. 9 occurring in any suitable order. Moreover, although this disclosure describes and illustrates an example method for storing a compressed digital image including the particular steps of the method of FIG. 9, this disclosure contemplates any suitable method for storing a compressed digital image including any suitable steps, which can include all, some, or none of the steps of the method of FIG. 9, where appropriate. Furthermore, although this disclosure describes and illustrates particular components, devices, or systems carrying out particular steps of the method of FIG. 9, this disclosure contemplates any suitable combination of any suitable components, devices, or systems carrying out any suitable steps of the method of FIG. 9.

Figure 10:
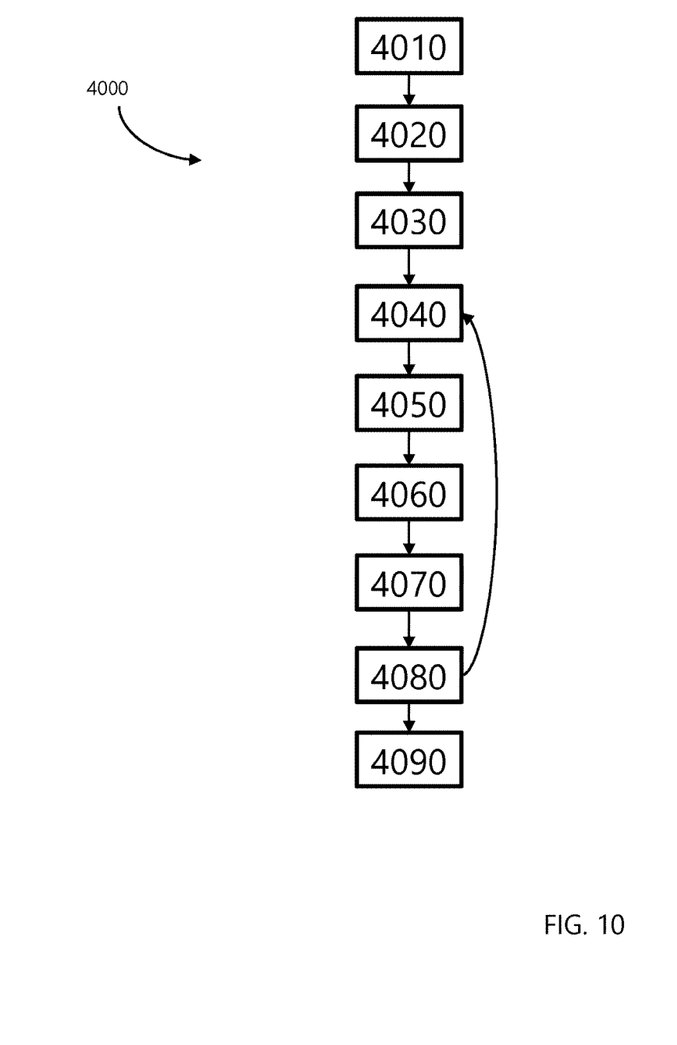
FIG. 10 is a flow chart of a method for storing a compressed digital image in accordance with the disclosed subject matter.

FIG. 10 illustrates an example method 4000 for storing a compressed digital image. The method can include loops and if/then statements to proceed efficiently. For example, the method can being at step 4010, where the method includes receiving, at one or more computing devices, a digital image. At step 4020 the method can include performing, at the one or more computing devices, an AI diagnostic test on the digital image. At step 4030 the method can include determining, at the one or more computing devices, an uncompressed diagnostic result associated with the digital image based on the AI diagnostic test. At step 4040 the method can include generating, at the one or more computing devices, a first compressed digital image by compressing the digital image. At step 4050 the method can include decompressing, at the one or more computing devices, the compressed digital image to generate a decompressed digital image. At step 4060 the method can include performing, at the one or more computing devices, the AI diagnostic test on the first decompressed digital image. At step 4070 the method can include determining, at the one or more computing devices, a decompressed diagnostic result associated with the first decompressed digital image based on the AI diagnostic test. At step 4080 the method can include determining whether the decompressed diagnostic result is the same as the uncompressed diagnostic result. If the result is the same, the method can include storing decompressed digital image as a selected decompressed digital image, return to step 4040 and proceed to generate a next compressed digital image by compressing the digital image. Each time a next compressed digital image is created, the next compressed digital image can have an increased compression ratio. If the result is not the same, the method can proceed to step 4090. At step 4090, the method can include storing, at the one or more computing devices, the compressed digital image associated with the selected decompressed digital image. In accordance with the disclosed subject matter, the method can repeat one or more steps of the method of FIG. 10, where appropriate. Although this disclosure describes and illustrates particular steps of the method of FIG. 10 as occurring in a particular order, this disclosure contemplates any suitable steps of the method of FIG. 10 occurring in any suitable order. Moreover, although this disclosure describes and illustrates an example method for storing a compressed digital image including the particular steps of the method of FIG. 10, this disclosure contemplates any suitable method for storing a compressed digital image including any suitable steps, which can include all, some, or none of the steps of the method of FIG. 10, where appropriate. Furthermore, although this disclosure describes and illustrates particular components, devices, or systems carrying out particular steps of the method of FIG. 10, this disclosure contemplates any suitable combination of any suitable components, devices, or systems carrying out any suitable steps of the method of FIG. 10.

In accordance with the disclosed subject matter, although methods 3000 and 4000 generally describe starting with the smallest compression ratio and performing compressions with increasing compression during each loop to identify the first compression method that does not have the same uncompressed and compressed diagnostic results, methods 3000 and 4000 can include starting with the highest compression ratio and performing compressions with decreasing compression during each loop to identify the first compression method that does have the same uncompressed and compressed diagnostic results.

As described above in connection with certain embodiments, certain components, e.g., server 30 and workstation 60, can include a computer or computers, processor, network, mobile device, cluster, or other hardware to perform various functions. Moreover, certain elements of the disclosed subject matter can be embodied in computer readable code which can be stored on computer readable media and which when executed can cause a processor to perform certain functions described herein. In these embodiments, the computer and/or other hardware play a significant role in permitting the system and method for displaying medical image records. For example, the presence of the computers, processors, memory, storage, and networking hardware provides the ability to display medical image records in a more efficient manner. Moreover, storing and saving the digital records cannot be accomplished with pen or paper, as such information is received over a network in electronic form.

The subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or may be included in, one or more separate physical components or media (e.g., multiple CDs, disks, or other storage devices).

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA or an ASIC. The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program can, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA or an ASIC.

Processors suitable for the execution of a computer program can include, by way of example and not by way of limitation, both general and special purpose microprocessors. Devices suitable for storing computer program instructions and data can include all forms of non-volatile memory, media and memory devices, including by way of example but not by way of limitation, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Additionally, as described above in connection with certain embodiments, certain components can communicate with certain other components, for example via a network, e.g., a local area network or the internet. To the extent not expressly stated above, the disclosed subject matter is intended to encompass both sides of each transaction, including transmitting and receiving. One of ordinary skill in the art will readily understand that with regard to the features described above, if one component transmits, sends, or otherwise makes available to another component, the other component will receive or acquire, whether expressly stated or not.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method of storing a compressed digital image, comprising:
receiving, at one or more computing devices, a digital image;
performing, at the one or more computing devices, an artificial intelligence ("AI") diagnostic test on the digital image;
determining, at the one or more computing devices, an uncompressed diagnostic result associated with the digital image based on the AI diagnostic test;
generating, at the one or more computing devices, one or more compressed digital images by compressing the digital image, each compressed digital image having a respective compression ratio;
decompressing, at the one or more computing devices, each compressed digital image to generate a respective decompressed digital image;
performing, at the one or more computing devices, the AI diagnostic test on each decompressed digital image;
determining, at the one or more computing devices, a decompressed diagnostic result associated with each decompressed digital image based on the respective AI diagnostic test;
identifying, at the one or more computing devices, one or more decompressed digital images having a respective decompressed diagnostic result that is the same as the uncompressed diagnostic result;
selecting, at the one or more computing devices and from the identified one or more decompressed digital images, the decompressed digital image associated with the highest compression ratio; and
storing, at the one or more computing devices, the compressed digital image associated with the selected decompressed digital image.

2. The method of claim 1, wherein the digital record comprises a medical image record.

3. The method of claim 2, wherein the medical image record comprises a Digital Imaging and Communications in Medicine ("DICOM") Service-Object Pair Instance.

4. The method of claim 1, wherein each compressed digital image is generated using a respective loss-less or lossy compression technique.

5. The method of claim 1, wherein for each compressed digital image, the compression ratio is calculated by dividing an uncompressed file size of the uncompressed image by a compressed file size of the compressed digital image.

6. The method of claim 1, further comprising deleting the digital image.

7. The method of claim 1, further comprising deleting the selected decompressed digital image.

8. The method of claim 1, further comprising deleting each non-selected decompressed digital image and each associated compressed digital image.

9. One or more computer readable non-transitory storage media embodying software that is operable when executed to:
receive a digital image;
perform an artificial intelligence ("AI") diagnostic test on the digital image;
determine an uncompressed diagnostic result associated with the digital image based on the AI diagnostic test;
generate one or more compressed digital images by compressing the digital image, each compressed digital image having a respective compression ratio;
decompress each compressed digital image to generate a respective decompressed digital image;
perform the AI diagnostic test on each decompressed digital image;
determine a decompressed diagnostic result associated with each decompressed digital image based on the respective AI diagnostic test;
identify one or more decompressed digital images having a respective decompressed diagnostic result that is the same as the uncompressed diagnostic result;
select from the identified one or more decompressed digital images, the decompressed digital image associated with the highest compression ratio; and
store the compressed digital image associated with the selected decompressed digital image.

10. The media of claim 9, wherein the digital record comprises a medical image record.

11. The media of claim 10, wherein the medical image record comprises a Digital Imaging and Communications in Medicine ("DICOM") Service-Object Pair Instance.

12. The media of claim 9, wherein each compressed digital image is generated using a respective loss-less or lossy compression technique.

13. The media of claim 9, wherein for each compressed digital image, the compression ratio is calculated by dividing an uncompressed file size of the uncompressed image by a compressed file size of the compressed digital image.

14. The media of claim 9, further comprising deleting the digital image.

15. The media of claim 9, further comprising deleting the selected decompressed digital image.

16. The media of claim 9, further comprising deleting each non-selected decompressed digital image and each associated compressed digital image.

17. A system comprising: one or more processors; and a memory coupled to the processors comprising instructions executable by the processors, the processors being operable when executing the instructions to:

receive a digital image;

perform an artificial intelligence ("AI") diagnostic test on the digital image;

determine an uncompressed diagnostic result associated with the digital image based on the AI diagnostic test;

generate one or more compressed digital images by compressing the digital image, each compressed digital image having a respective compression ratio;

decompress each compressed digital image to generate a respective decompressed digital image;

perform the AI diagnostic test on each decompressed digital image;

determine a decompressed diagnostic result associated with each decompressed digital image based on the respective AI diagnostic test;

identify one or more decompressed digital images having a respective decompressed diagnostic result that is the same as the uncompressed diagnostic result;

select from the identified one or more decompressed digital images, the decompressed digital image associated with the highest compression ratio; and store the compressed digital image associated with the selected decompressed digital image.

18. The system of claim 17, wherein the digital record comprises a medical image record.

19. The system of claim 18, wherein the medical image record comprises a Digital Imaging and Communications in Medicine ("DICOM") Service-Object Pair Instance.

20. The system of claim 17, wherein each compressed digital image is generated using a respective loss-less or lossy compression technique.

21. The system of claim 17, wherein for each compressed digital image, the compression ratio is calculated by dividing an uncompressed file size of the uncompressed image by a compressed file size of the compressed digital image.

22. The system of claim 17, further comprising deleting the digital image.

23. The system of claim 17, further comprising deleting the selected decompressed digital image.

24. The system of claim 17, further comprising deleting each non-selected decompressed digital image and each associated compressed digital image.

* * * * *